(12) United States Patent
Jukes et al.

(10) Patent No.: US 10,130,483 B2
(45) Date of Patent: Nov. 20, 2018

(54) TIBIAL COMPONENT WITH ENHANCED RADIAL CEMENT FIXATION

(71) Applicant: ZIMMER GMBH, Winterthur (CH)

(72) Inventors: Andrew J. Jukes, Wetzikon (CH);
Rosemary E. Thompson, Elgg (CH);
Jorg Zimmermann, Winterthur (CH)

(73) Assignee: Zimmer GmbH, Winterthur (CH)

( * ) Notice: Subject to any disclaimer, the term of this patent is extended or adjusted under 35 U.S.C. 154(b) by 0 days.

(21) Appl. No.: 15/493,598

(22) Filed: Apr. 21, 2017

(65) Prior Publication Data

US 2017/0216039 A1  Aug. 3, 2017

Related U.S. Application Data

(63) Continuation of application No. 12/868,110, filed on Aug. 25, 2010, now Pat. No. 9,655,731.

(60) Provisional application No. 61/236,988, filed on Aug. 26, 2009.

(51) Int. Cl.
*A61F 2/38* (2006.01)
*A61F 2/30* (2006.01)

(52) U.S. Cl.
CPC ............ *A61F 2/389* (2013.01); *A61F 2/3886* (2013.01); *A61F 2002/305* (2013.01); *A61F 2002/30011* (2013.01); *A61F 2002/30449* (2013.01); *A61F 2002/30487* (2013.01); *A61F 2002/30981* (2013.01); *A61F 2310/00035* (2013.01); *A61F 2310/00131* (2013.01)

(58) Field of Classification Search
CPC ....................................................... A61F 2/38
See application file for complete search history.

(56) References Cited

U.S. PATENT DOCUMENTS

| 5,019,103 | A | 5/1991 | Van Zile et al. |
|---|---|---|---|
| 5,152,797 | A | 10/1992 | Luckman et al. |
| 5,443,512 | A | 8/1995 | Parr et al. |
| 5,658,334 | A | 8/1997 | Caldarise et al. |
| 6,599,322 | B1 | 7/2003 | Amrich et al. |
| 7,018,418 | B2 | 3/2006 | Amrich et al. |
| 8,628,580 | B2 | 1/2014 | Sanford et al. |
| 9,408,702 | B2 | 8/2016 | Metzger |
| 2004/0162619 | A1 | 8/2004 | Blaylock et al. |
| 2006/0178749 | A1 | 8/2006 | Pendleton et al. |
| 2008/0027556 | A1 | 1/2008 | Metzger |
| 2009/0084491 | A1 | 4/2009 | Uthgenannt et al. |
| 2009/0099663 | A1 | 4/2009 | Romagnoli |
| 2009/0216325 | A1 | 8/2009 | May et al. |
| 2009/0281583 | A1 | 11/2009 | Brown et al. |

(Continued)

FOREIGN PATENT DOCUMENTS

WO  WO-2007090784 A1  8/2007

OTHER PUBLICATIONS

"U.S. Appl. No. 12/868,110, Advisory Action dated May 11, 2016", 2 pgs.

(Continued)

*Primary Examiner* — Matthew Schall
(74) *Attorney, Agent, or Firm* — Schwegman Lundberg & Woessner, P.A.

(57) ABSTRACT

A cemented tibial prosthesis having a bone-contacting surface with a porous outer rim. With the bone-contacting surface seated against a resected proximal tibia, bone cement or another suitable adhesive will travel into the pores of the porous outer rim to enhance the connection between the tibial prosthesis and the tibia.

18 Claims, 3 Drawing Sheets

(56) References Cited

U.S. PATENT DOCUMENTS

| | | |
|---|---|---|
| 2010/0004754 A1 | 1/2010 | Brown et al. |
| 2010/0076566 A1 | 3/2010 | Serafin, Jr. et al. |
| 2010/0100190 A1 | 4/2010 | May et al. |
| 2010/0100191 A1 | 4/2010 | May et al. |
| 2011/0098824 A1 | 4/2011 | Jukes et al. |

OTHER PUBLICATIONS

"U.S. Appl. No. 12/868,110, Final Office Action dated Jan. 5, 2016", 7 pgs.
"U.S. Appl. No. 12/868,110, Final Office Action dated Nov. 29, 2013", 6 pgs.
"U.S. Appl. No. 12/868,110, Non Final Office Action dated Jun. 22, 2012", 5 pgs.
"U.S. Appl. No. 12/868,110, Notice of Allowance dated Jan. 20, 2017", 7 pgs.
"U.S. Appl. No. 12/868,110, Response dated Feb. 10, 2012 to Restriction Requirement dated Dec. 13, 2011", 3 pgs.
"U.S. Appl. No. 12/868,110, Response dated Apr. 5, 2016 to Non-Final Office Action dated Jan. 5, 2016", 9 pgs.
"U.S. Appl. No. 12/868,110, Response dated May 27, 2014 to Final Office Action dated Nov. 29, 2013", 10 pgs.
"U.S. Appl. No. 12/868,110, Response dated Oct. 22, 2012 to Non Final Office Action dated Jun. 22, 2012", 9 pgs.
"U.S. Appl. No. 12/868,110, Restriction Requirement dated Dec. 13, 2011", 6 pgs.
"Zimmer NexGen MIS Tibial Component Cemented Surgical Technique", Zimmer, Inc, #97-5950-002-00 Rev.1 1.5ML, (2005), 14 pgs.

TIBIAL COMPONENT WITH ENHANCED RADIAL CEMENT FIXATION

CROSS REFERENCE TO RELATED APPLICATION

This application is a continuation of U.S. patent application Ser. No. 12/868,110, entitled "TIBIAL COMPONENT WITH ENHANCED RADIAL CEMENT FIXATION," filed Aug. 25, 2010, which claims priority from U.S. Provisional Patent Application Ser. No. 61/236,988, entitled "TIBIAL COMPONENT WITH ENHANCED RADIAL CEMENT FIXATION," filed Aug. 26, 2009, the disclosures of which are hereby expressly incorporated by reference herein in its entirety.

BACKGROUND

1. Field of the Invention

The present invention relates to the field of orthopedics. More particularly, the present invention relates to a cemented tibial prosthesis, and to a method for using the same.

2. Description of the Related Art

Orthopedic prostheses are commonly used to repair and replace damaged bone and tissue in the human body. For example, to repair damaged bone of the knee joint and to recreate the natural, anatomical articulation of the knee joint, a tibial prosthesis may be implanted in the proximal tibia and/or a femoral prosthesis may be implanted in the distal femur.

The tibial prosthesis may include a first, articulating component having a concave articulating surface configured for articulation against a natural femur or a femoral prosthesis. The tibial prosthesis may also include a second, tray component having a bone-contacting surface configured for securing the tibial prosthesis to the bone stock of a resected proximal tibia. The articulating component may be made from a polymer to facilitate articulation with the adjacent femoral prosthesis, while the tray component may be made from a metal to provide additional strength and rigidity to the tibial prosthesis.

SUMMARY

The present invention provides a cemented tibial prosthesis having a bone-contacting surface with a porous outer rim. With the bone-contacting surface seated against a resected proximal tibia, bone cement or another suitable adhesive will travel into the pores of the porous outer rim to enhance the connection between the tibial prosthesis and the tibia.

According to an embodiment of the present invention, a tibial prosthesis is provided that is configured for securement to a patient's tibia and for articulation with an adjacent femoral component. The tibial prosthesis includes an articulating component and a tray component. The articulating component has a concave articulating surface to facilitate articulation with the femoral component. The tray component is coupled to the articulating component, the tray component having a bone-contacting surface that is configured for securement to the patient's tibia, the bone-contacting surface having an outer edge, the bone-contacting surface including an interior region and an outer porous region, the outer porous region of the bone-contacting surface having a higher porosity than the interior region of the bone-contacting surface, the outer porous region of the bone-contacting surface extending along the outer edge to at least partially surround the interior region of the bone-contacting surface.

According to another embodiment of the present invention, a tibial prosthesis is provided that is configured for securement to a patient's tibia and for articulation with an adjacent femoral component. The tibial prosthesis includes an articulating component and a tray component. The articulating component has a concave articulating surface to facilitate articulation with the femoral component. The tray component is coupled to the articulating component, the tray component having a bone-contacting surface that is configured for securement to the patient's tibia and at least one anchor that extends distally from the bone-contacting surface, the bone-contacting surface including an interior region and an outer porous region, the outer porous region of the bone-contacting surface having a higher porosity than the interior region of the bone-contacting surface and being spaced further from the at least one anchor than the interior region of the bone-contacting surface.

According to yet another embodiment of the present invention, a tibial prosthesis is provided for securement to a resected surface of a patient's tibia and for articulation with an adjacent femoral component, the resected surface of the patient's tibia having an interior area and a peripheral area surrounding the interior area. The tibial prosthesis includes an articulating component and a tray component having a bone-contacting surface with an interior region and an outer porous region, the outer porous region of the bone-contacting surface having a higher porosity than the interior region of the bone-contacting surface, the tibial prosthesis configured for securement to the patient's tibia with the bone-contacting surface of the tray component facing the resected surface of the patient's tibia, the interior region of the bone-contacting surface facing the interior area of the resected surface and the outer porous region of the bone-contacting surface facing the peripheral area of the resected surface and surrounding a majority of the interior area of the resected surface.

BRIEF DESCRIPTION OF THE DRAWINGS

The above-mentioned and other features and advantages of this invention, and the manner of attaining them, will become more apparent and the invention itself will be better understood by reference to the following description of embodiments of the invention taken in conjunction with the accompanying drawings, wherein.

Corresponding reference characters indicate corresponding parts throughout the several views. The exemplifications set out herein illustrate exemplary embodiments of the invention and such exemplifications are not to be construed as limiting the scope of the invention in any manner.

DETAILED DESCRIPTION

Figure 1:
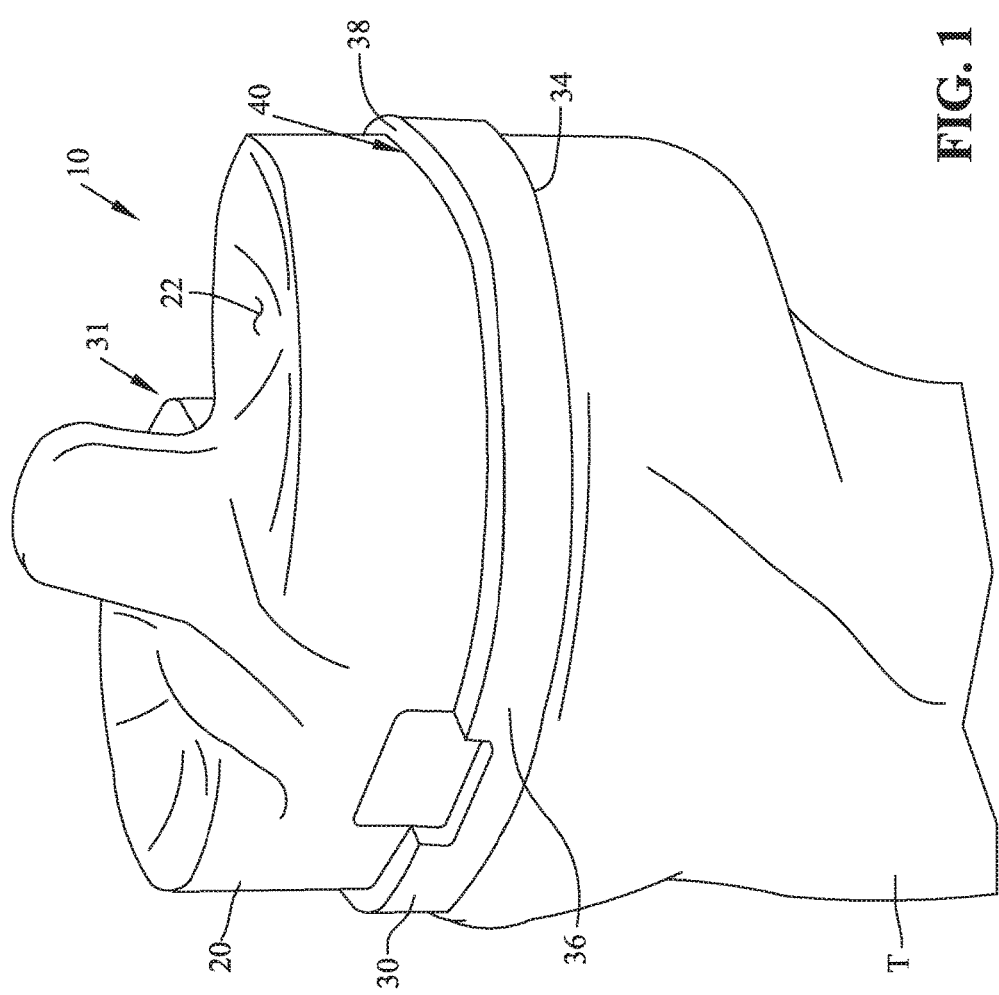
FIG. 1 is a proximal perspective view of an exemplary tibial prosthesis of the present invention implanted in a resected proximal tibia, the tibial prosthesis including a first, articulating component mounted atop a second, tray component.

Referring to FIG. 1, an exemplary tibial prosthesis 10 is shown implanted in a resected proximal tibia T. Tibial prosthesis 10 includes a first, articulating component 20 mounted atop a second, tray component 30.

As shown in FIG. 1, articulating component 20 of tibial prosthesis 10 includes at least one concave articulating surface 22 configured for articulation against a natural femur (not shown) or a femoral prosthesis (not shown). To facilitate articulation with an adjacent femoral component, articulating component 20 of tibial prosthesis 10 may be constructed of a smooth, abrasion-resistant material. Also, to provide cushioning to the knee joint, articulating component 20 of tibial prosthesis 10 may be constructed of a resilient, deformable material. For example, articulating component 20 may be constructed of a biocompatible polymer, including, but not limited to, a hydrogel, poly ether ether ketone, fiber reinforced poly ether ether ketone, ultrahigh molecular weight polyethylene, crosslinked ultrahigh molecular weight polyethylene, or polyether ketone ether ether ketone. It is also within the scope of the present invention that articulating component 20 may be constructed of a more rigid material like a biocompatible ceramic. Suitable ceramics include oxide ceramics, such as alumina or zirconia, and non-oxide ceramics, such as silicon nitride or silicon carbide.

Figure 2:
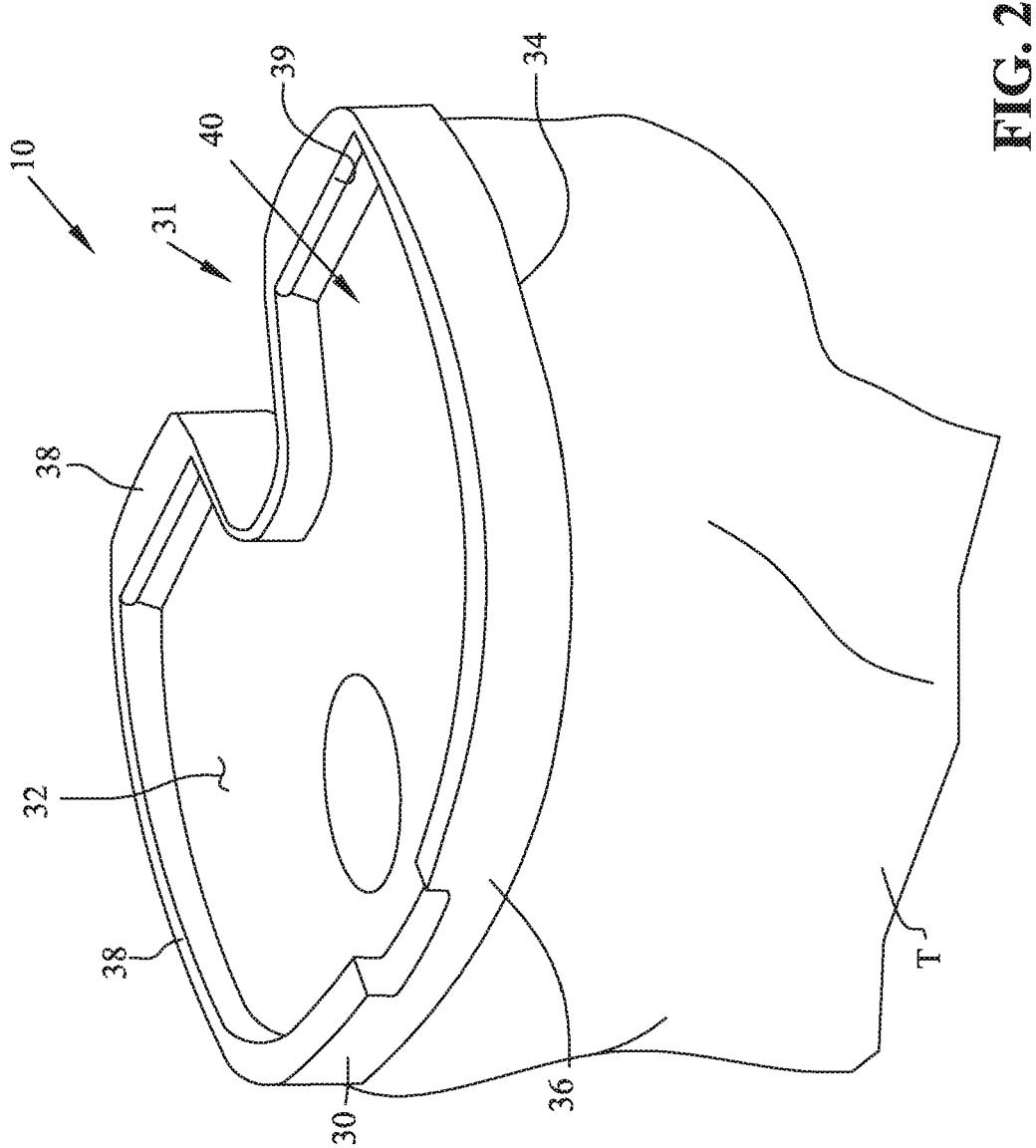
FIG. 2 is a proximal perspective view similar to FIG. 1 of the tray component implanted in the resected proximal tibia, the tibial prosthesis shown without the articulating component mounted atop the tray component.
Figure 3:
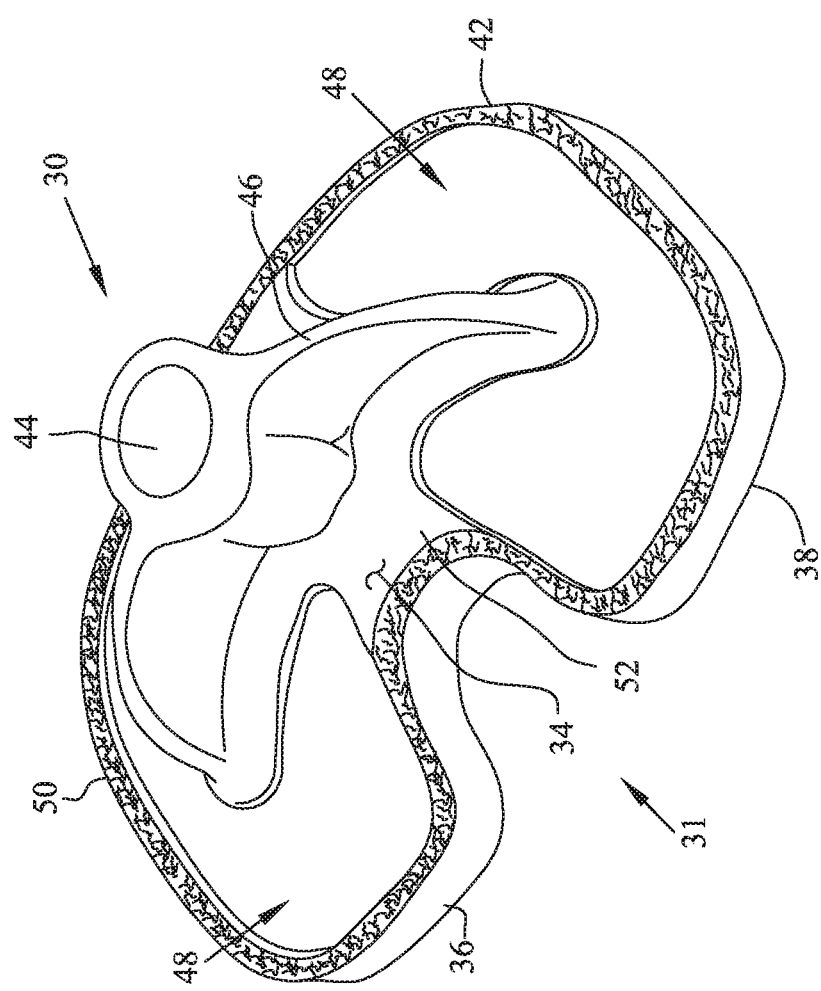
FIG. 3 is a distal perspective view of the tray component of FIG. 1.

Referring next to FIGS. 2 and 3, tray component 30 of tibial prosthesis 10 is substantially U-shaped with posterior recess 31 being sized and shaped to receive the patient's posterior cruciate ligament (PCL). Tray component 30 of tibial prosthesis 10 includes a substantially planar, proximal receiving surface 32 and a substantially planar, distal bone-contacting surface 34 located opposite receiving surface 32. Tray component 30 of tibial prosthesis 10 also includes peripheral wall 36 that extends between receiving surface 32 and bone-contacting surface 34. As shown in FIG. 3, bone-contacting surface 34 of tray component 30 is substantially U-shaped, having outer edge 42 that borders peripheral wall 36.

To provide strength and rigidity to tibial prosthesis 10, tray component 30 may be constructed of a rigid biocompatible ceramic or metal. For example, tray component 30 may be constructed of titanium, a titanium alloy, a zirconium alloy, tantalum, cobalt chromium, or cobalt chromium molybdenum.

As shown in FIG. 2, receiving surface 32 of tray component 30 is configured to receive and mate with articulating component 20 (FIG. 1). Peripheral wall 36 of tray component 30 extends proximally beyond receiving surface 32 to define an outer rim or lip 38. Receiving surface 32 and rim 38 of tray component 30 cooperate to define chamber 40. According to an exemplary embodiment of the present invention, when articulating component 20 is received within chamber 40 of tray component 30 as shown in FIG. 1, articulating component 20 rests against receiving surface 32 of tray component 30 and is supported externally by rim 38 of tray component 30.

Articulating component 20 may be attached to tray component 30 via an interference fit, with a mechanical fastener, or with an adhesive, for example. Also, some or all portions of rim 38 may include flange 39 that projects inwardly into chamber 40. In this embodiment, articulating component 20 may include a groove (not shown) that is sized to receive flange 39 of rim 38 in a tongue and groove arrangement to prevent articulating component 20 from lifting off of tray component 30.

As shown in FIG. 3, bone-contacting surface 34 of tray component 30 is configured for securement to the bone stock of a resected proximal tibia T (FIG. 2). An exemplary attachment method involves using an adhesive, such as bone cement, which may not only provide a secure connection between tray component 30 and tibia T, but may also strengthen tibia T. The adhesive may be any known medical grade adhesive having sufficient strength to secure tray component 30 to tibia T, including, but not limited to, light curable acrylic adhesives, acrylic adhesives, cyanoacrylate adhesives, silicone adhesives, urethane adhesives, epoxy adhesives, and bone cement.

Tray component 30 includes stem 44 and keel 46 that extend distally from the center of bone-contacting surface 34, as shown in FIG. 3. In operation, with bone-contacting surface 34 of tray component 30 seated against the resected proximal tibia T (FIG. 2), stem 44 and keel 46 of tray component 30 extend into the intramedullary canal of tibia T to stabilize tray component 30 and to prevent rotation of tray component 30 relative to tibia T. The intramedullary canal of tibia T may be filled with bone cement or another suitable adhesive to anchor stem 44 and keel 46 in place.

Tray component 30 further includes pockets 48 that are recessed into bone-contacting surface 34, as shown in FIG. 3. In operation, with bone-contacting surface 34 of tray component 30 seated against the resected proximal tibia T (FIG. 2), pockets 48 of tray component 30 provide gaps between tray component 30 and tibia T for receiving bone cement or another suitable adhesive.

As shown in FIG. 3, bone-contacting surface 34 of tray component 30 includes porous outer rim 50 that substantially or entirely surrounds tray component 30 along outer edge 42. In this embodiment, bone-contacting surface 34 of tray component 30 is cooperatively defined by porous outer rim 50 and a solid or non-porous interior region 52 that is less porous than porous outer rim 50. Porous outer rim 50 may include a strip of porous material that is inlayed into and bonded to tray component 30, such that porous outer rim 50 is generally flush with non-porous interior region 52 of bone-contacting surface 34. In the illustrated embodiment of FIG. 3, porous outer rim 50 is radially spaced from non-porous interior region 52 of bone-contacting surface 34, and from stem 44, keel 46, and pockets 48, that extend distally from or proximally into non-porous interior region 52 of bone-contacting surface 34, all of which are more centrally located on tray component 30 than porous outer rim 50. In operation, with bone-contacting surface 34 of tray component 30 seated against the resected proximal tibia T (FIG. 2), bone cement or another suitable adhesive will travel into the pores of porous outer rim 50 to enhance the connection between tray component 30 and tibia T, especially along outer edge 42 of bone-contacting surface 34.

According to an exemplary embodiment of the present invention, porous outer rim 50 extends entirely to outer edge 42 of bone-contacting surface 34. It is also within the scope of the present invention that porous outer rim 50 may be spaced apart slightly from outer edge 42 of bone-contacting surface 34 while still being considered to extend along outer edge 42 of bone-contacting surface 34. For example, porous outer rim 50 may be spaced apart from outer edge 42 of bone-contacting surface 34 by approximately 1 mm, 2 mm, or 3 mm.

The width of porous outer rim 50 may vary depending upon the size of tray component 30 and/or the needs of a particular patient. In certain embodiments, porous outer rim 50 may have a width as small as approximately 1 mm, 3 mm, or 5 mm and as large as approximately 10 mm, 13 mm, 15 mm, or more. It is also within the scope of the present invention that the width of porous outer rim 50 may vary across the perimeter of tray component 30. For example, the medial/lateral width of porous outer rim 50 may exceed the anterior/posterior width of porous outer rim 50.

Porous outer rim 50 of bone-contacting surface 34 may account for approximately 3%, 5%, 10%, 15%, 20%, or more of the total underside surface area of tray component 30, with non-porous interior region 52 of bone-contacting surface 34, stem 44, keel 46, and pockets 48, accounting for the remaining 80%, 85%, 90%, 95%, or 97% of the underside surface area of tray component 30.

The present inventors have recognized that traction forces and pulsing forces on tibial prosthesis 10 reach a maximum level along peripheral wall 36 and rim 38 of tray component 30. Due to these high forces along peripheral wall 36 and rim 38 of tray component 30, the present inventors have observed from X-rays that implanted tray components 30 begin detaching from the bone stock of tibia T and the adhesive layer along the adjacent outer edge 42 of bone-contacting surface 34. Porous outer rim 50 of the present invention may strengthen the connection between tray component 30 and tibia T, especially along outer edge 42 of bone-contacting surface 34, to prevent such separation from tibia T when tray component 30 is exposed to anatomical forces. Also, the material cost of tray component 30 having porous outer rim 50 may be less than the material cost of tray component 30 that is completely coated with or constructed entirely of a porous material. Moreover, because bone-contacting surface 34 of tray component 30 may include non-porous interior region 52 and cement pockets 48, a surgeon should not mistake tray component 30 for a non-cemented prosthesis that may be attached to tibia T primarily via bone ingrowth.

Porous outer rim 50 of tray component 30 may be constructed of a porous material having adequately sized pores for receiving bone cement or another suitable adhesive. For example, porous outer rim 50 may include a beaded material, a woven material, or a wire mesh material. An exemplary metallic wire mesh material includes Sulmesh generally available from Zimmer GmbH of Winterthur, Switzerland. Such materials may be less expensive than highly porous biomaterials designed to encourage bone ingrowth. However, it is within the scope of the present invention that porous outer rim 50 may be constructed of a highly porous biomaterial. An exemplary highly porous biomaterial is produced using Trabecular Metal™ technology generally available from Zimmer, Inc., of Warsaw, Ind. Trabecular Metal™ is a trademark of Zimmer, Inc. Such a material may be formed from a reticulated vitreous carbon foam substrate which is infiltrated and coated with a biocompatible metal, such as tantalum, by a chemical vapor deposition ("CVD") process in the manner disclosed in detail in U.S. Pat. No. 5,282,861, the disclosure of which is expressly incorporated herein by reference.

While this invention has been described as having preferred designs, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A tibial prosthesis configured for securement to a patient's tibia and for articulation with an adjacent femoral component, the tibial prosthesis comprising:
   an articulating component having a concave articulating surface to facilitate articulation with the femoral component; and
   a tray component comprising:
     a proximal receiving surface, to which the articulating component is coupled;
     a distal bone-contacting surface opposite the receiving surface, the bone-contacting surface comprising:
       a porous outer rim;
       a non-porous interior region arranged medially on the bone-contacting surface, from which an anchor extends distally; and
       at least one non-porous cement pocket interposed between the porous outer rim and the non-porous interior region on a lateral side of the non-porous interior region,
       the porous outer rim completely surrounding a radially inner region of the bone-contacting surface comprising both the non-porous interior region and the at least one non-porous cement pocket, and
       the porous outer rim having a higher porosity than the non-porous interior region and the at least one non-porous cement pocket.

2. The tibial prosthesis of claim 1, wherein the at least one non-porous cement pocket comprises two non-porous cement pockets, one of the two non-porous cement pockets interposed between the porous outer rim and the non-porous interior region on a first lateral side of the non-porous interior region and the other of the two non-porous cement pockets interposed between the porous outer rim and the non-porous interior region on a second lateral side of the non-porous interior region.

3. The tibial prosthesis of claim 1, wherein the at least one non-porous cement pocket is recessed proximally relative to the porous outer rim and the non-porous interior region of the bone-contacting surface.

4. The tibial prosthesis of claim 1, wherein at least a portion of the at least one non-porous cement pocket is directly bordered by the porous outer rim of the bone-contacting surface.

5. The tibial prosthesis of claim 1, wherein the non-porous interior region and the porous outer rim of the bone-contacting surface are substantially flush to define a substantially planar bone-contacting surface.

6. The tibial prosthesis of claim 1, wherein the porous outer rim of the bone-contacting surface has a width between approximately 1 mm and 15 mm.

7. The tibial prosthesis of claim 1, wherein the porous outer rim accounts for approximately between 3% and 20% of a total surface area of the bone-contacting surface of the tray component.

8. The tibial prosthesis of claim 1, wherein the porous outer rim of the bone-contacting surface has a varying width along a perimeter of the tray component.

9. The tibial prosthesis of claim 1, wherein the porous outer rim includes tantalum.

10. A tray component for a tibial prosthesis configured for securement to a patient's tibia and for articulation with an adjacent femoral component, the tray component comprising:
    a proximal receiving surface configured to receive and be coupled to an articulating component having a concave bearing surface;
    a distal bone-contacting surface opposite the receiving surface, the bone-contacting surface comprising:
      a high-porosity outer rim;

a low-porosity interior region arranged medially on the bone-contacting surface, from which an anchor extends distally; and at least one low-porosity cement pocket interposed between the high-porosity outer rim and the low-porosity interior region on a lateral side of the low-porosity interior region, the high-porosity outer rim completely surrounding a radially inner region of the bone-contacting surface comprising both the low-porosity interior region and the at least one low-porosity cement pocket, and the high-porosity outer rim having a higher porosity than the low-porosity interior region and the at least one low-porosity cement pocket.

11. The tray component of claim 10, wherein the at least one low-porosity cement pocket comprises two low-porosity cement pockets, one of the two low-porosity cement pockets interposed between the high-porosity outer rim and the low-porosity interior region on a first lateral side of the low-porosity interior region and the other of the two low-porosity cement pockets interposed between the high-porosity outer rim and the low-porosity interior region on a second lateral side of the low-porosity interior region.

12. The tray component of claim 10, wherein the at least one low-porosity cement pocket is recessed proximally relative to the high-porosity outer rim and the low-porosity interior region of the bone-contacting surface.

13. The tray component of claim 10, wherein at least a portion of the at least one low-porosity cement pocket is directly bordered by the high-porosity outer rim of the bone-contacting surface.

14. The tray component of claim 10, wherein the low-porosity interior region and the high-porosity outer rim of the bone-contacting surface are substantially flush to define a substantially planar bone-contacting surface.

15. The tray component of claim 10, wherein the high-porosity outer rim of the bone-contacting surface has a width between approximately 1 mm and approximately 15 mm.

16. The tray component of claim 10, wherein the high-porosity outer rim accounts for approximately between 3% and 20% of a total surface area of the bone-contacting surface of the tray component.

17. The tray component of claim 10, wherein the high-porosity outer rim of the bone-contacting surface has a varying width along a perimeter of the tray component.

18. The tray component of claim 10, wherein the high-porosity outer rim includes tantalum.

* * * * *